(12) United States Patent
Abram

(10) Patent No.: US 6,730,288 B1
(45) Date of Patent: May 4, 2004

(54) MOUSSE COMPOSITION

(75) Inventor: Albert Zorko Abram, Wantirna (AU)

(73) Assignee: Connetics Australia Pty Ltd, Rowville (AU)

( * ) Notice: Subject to any disclaimer, the term of this patent is extended or adjusted under 35 U.S.C. 154(b) by 0 days.

(21) Appl. No.: 09/719,662

(22) PCT Filed: Sep. 8, 1999

(86) PCT No.: PCT/AU99/00735

§ 371 (c)(1),
(2), (4) Date: Jan. 30, 2001

(87) PCT Pub. No.: WO00/15193

PCT Pub. Date: Mar. 23, 2000

(30) Foreign Application Priority Data

Sep. 11, 1998 (AU) ................................. PP5831

(51) Int. Cl.⁷ .......................... A61K 9/12; A61K 9/10; A61K 9/00; A01N 25/04; A01N 25/06
(52) U.S. Cl. ...................... 424/45; 424/78.03; 424/401; 424/59; 514/730; 514/846; 514/859; 514/861; 514/887; 514/945; 514/947; 128/200.23
(58) Field of Search ................................. 424/45, 78.03, 424/401, 59; 128/200.23; 514/730, 846, 859, 861, 887, 945, 947

(56) References Cited

U.S. PATENT DOCUMENTS 5,143,717 A 9/1992 Davis ........................ 424/45

FOREIGN PATENT DOCUMENTS

| GB | 2327344 | 1/1999 |
| WO | WO 96/27376 | 9/1996 |
| WO | 9904751 | 2/1999 |

OTHER PUBLICATIONS

Woodford et al., Bioavailability and Activity of Topical Corticosteroids from a Novel Drug Delivery System, the Aerosol Quick–Break Foam, Journal of Pharmaceutical Sciences, vol. 66, No. 1, Jan. 1977, pp. 99–104.*

* cited by examiner

Primary Examiner—Frederick Krass
Assistant Examiner—Clinton T. Ostrup
(74) Attorney, Agent, or Firm—Townsend and Townsend and Crew LLP

(57) ABSTRACT

A pharmaceutical aerosol foam composition including an effective amount of a pharmaceutically active ingredient; an occlusive agent; an aqueous solvent; and an organic cosolvent, the pharmaceutically active ingredient being insoluble in both water and the occlusive agent; the occlusive agent being present in an amount sufficient to form an occlusive layer on the skin, in use.

40 Claims, 4 Drawing Sheets

MOUSSE COMPOSITION

The present invention provides a composition for the topical administration of pharmaceutical active ingredients.

Various aerosol and non-aerosol quick breaking and slow breaking foams for the topical delivery of pharmaceutical active ingredients are known in the prior art. In particular, the foam composition is an aqueous emulsion system. The foam composition upon actuation produces a stabilised, homogeneous, expandable foam which breaks easily with shear. A composition of this type is often referred to as an aerosol foam or "mousse".

It is known to use mousse compositions to topically deliver pharmaceutical active ingredients. An example of such a composition is in Australian patent application 80257/87 which discloses a mousse composition for the topical delivery of the pharmaceutically active ingredient, minoxidil. However the efficiency of such systems to deliver pharmaceutically active ingredients is limited.

Moreover, the majority of topical lotions and creams known or suggested in the prior art for delivering pharmaceutically active ingredients contain large amounts of petrolatum or some other occlusive agent to act as a barrier over the skin. This barrier reduces the evaporation of moisture from the skin which leads to increased moisture in the stratum corneum and in the epidermis and enhances the topical delivery of the pharmaceutical active ingredients.

However, in practice it would not be desirable to include such large amounts of an occlusive agent in a mousse formulation because when dispensed the mousse formulation would be a less stable foam, and upon application, the occlusive agent would leave a greasy, sticky lather on the skin which would not be considered acceptable to the consumer.

In prior art U.S. Pat. Nos. 5,002,680 and 4,981,677, there is disclosed mousse compositions that contain an occlusive agent such as petrolatum. These compositions are directed towards cosmetic purposes, and provide no disclosure on their suitability or otherwise to enhance the topical delivery of pharmaceutical active ingredients. Further, in respect of U.S. Pat. No. 4,981,677 the formulation includes a starch component. It is accordingly not apparent that an occlusive layer would be formed.

Accordingly, it would be a significant advance in the art if a mousse composition could be provided that enhanced the topical delivery of the pharmaceutical active ingredient while preferably still providing a pharmaceutically elegant and consumer acceptable composition.

in a first aspect of the present invention there is provided a pharmaceutical aerosol foam composition including an effective amount of a pharmaceutically active ingredient an occlusive agent an aqueous solvent; and an organic cosolvent;

the pharmaceutically active ingredient being insoluble in both water and the occlusive agent; the occlusive agent being present in an amount sufficient to form an occlusive layer on the skin, in use.

The present invention is predicated on the surprising discovery that a mousse formulation with a relatively low amount of an occlusive agent is still able to reduce trans epidermal water loss and hence in theory increase skin permeability to effect greater drug skin penetration while remaining an elegant and consumer acceptable composition.

The water-insoluble pharmaceutically active ingredient may be any suitable type. An analgesic such as capsaicin or piroxicam, antifungal such as clotrimazole or miconazole nitrate, antibacterial such as nitrofurazone or gramcidin, anaesthetic such as benzocaine or lidocaine, antiviral such as aciclovir or penciclovir, antipruritic such as crotamiton or phenol, antihistamine such as chlorpheniramine or triproldine, xanthine such as caffeine, sex hormone such as oestradiol or testosterone, anti-inflammatory agent or corticosteroid may be used. A corticosteroid is preferred. The corticosteroids may be selected from one or more of the group consisting of betamethasone valerate and clobetasol propionate. A corticosteroid is preferred. The corticosteroids may be selected from one or more of the group consisting of, betamethasone valerate and clobetasol propionate.

Clobetasol propionate is preferred.

The pharmaceutically active ingredient may be present in any effective amounts. The pharmaceutically active ingredient may be present in amounts of approximately 0.005% by weight to approximately 10% by weight, preferably approximately 0.05% to approximately 1% by weight, based on the total weight of the pharmaceutical aerosol foam composition.

The aerosol foam base can be made using compositions that are well known in the art.

The pharmaceutical aerosol foam composition may further include an effective amount of an aerosol propellant. The aerosol propellant used in the mousse composition may be any suitable gas, such as a hydrocarbon, e.g. propane, butane, CFCs, HFCs, nitrogen or air. In a preferred embodiment the aerosol propellant is a hydrocarbon. Where the aerosol propellant is a hydrocarbon it may be present in an amount of from approximately 2.5% to 20% by weight, preferably 2.5% to 7.5% by weight, based on the total weight of the pharmaceutical mousse composition. The propellant may be introduced into the mousse composition at the time of filling utilising for example a standard aerosol dispenser, e.g. a spray can arrangement.

The occlusive agent utilized in the pharmaceutical composition according to the present invention may be any excipient or combination thereof that provides an occlusive layer or hydration barrier to the skin. An occlusive layer or hydration barrier is a layer or barrier sufficient to result in reduction in trans epidermal water loss, which results in skin hydration. Suitable occlusive agents may be selected from one or more of the group consisting of mineral oils and greases, long chain acids, animal fats and greases, vegetable fats and greases, water insoluble polymers and the like. In a preferred embodiment the occlusive agent is petrolatum.

The occlusive agent is present in an amount sufficient to permit the formation of an occlusive layer or hydration barrier on the skin of the patient. Surprisingly applicants have discovered it is possible to form such an occlusive layer with a relatively low amount of occlusive agent. For example the amount of occlusive agent in the mousse composition may be up to approximately 55%, preferably approximately 40% or less by weight based on the total weight of the composition. In a preferred embodiment of the invention the amount of occlusive agent in the mousse composition may be up to approximately 50%, more preferably from approximately 20 to 50% by weight.

The pharmaceutical mousse composition may further include an effective amount of an emulsifier and/or surfactant.

The emulsifier or surfactant may be selected from one or more of the group consisting of non-ionic, anionic and cationic surfactants, e.g. fatty alcohols, fatty acids and fatty acid salts thereof.

Suitable emulsifiers or surfactants include pharmaceutically acceptable, non-toxic, non-ionic, anionic and cationic surfactants. Examples of suitable non-ionic surfactants include glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, and the like. Examples of suitable anionic surfactants are soaps including alkali soaps, such as sodium, potassium and ammonium salts of aliphatic carboxylic acids, usually fatty acids, such as sodium stearate. Organic amine soaps, also included, include organic amine salts of aliphatic carboxylic acids, usually fatty acids, such as triethanolamine stearate. Another class of suitable soaps is the metallic soaps, salts of polyvalent metals and aliphatic carboxylic acids, usually fatty acids, such as aluminium stearate. Other classes of suitable anionic surfactants include sulfated fatty acid alcohols such as sodium lauryl sulfate, sulfated oils such as the sulfuric ester of ricinoleic acid disodium salt, and sulfonated compounds such as alkyl sultonates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sulfonate such as aryl napthalene with alkyl substitutes. Examples of suitable cationic surfactants include amine salts such as octadecyl ammonium chloride, quartemary ammonium compounds such as benzalkonium chloride.

Surfactants which are a mixture of sorbitan monostearate and polysorbate 60 are preferred.

The emulsifier component may be present in any suitable stabilising amount. Preferably the emulsifier component may be in an amount where the ratio of emulsifier component to the occlusive agent, active pharmaceutical ingredient and cosolvent is about 1:5. The emulsifier component may be present in an amount of from approximately 1% to 15% by weight, preferably approximately 2.0% to 5.0% by weight, based on the total weight of the pharmaceutical mousse composition.

The aqueous solvent may be present in an amount of from approximately 25% to 95% by weight, preferably approximately 70% to 85% by weight, based on the total weight of the pharmaceutical mousse composition.

The composition further includes an organic cosolvent. The organic solvent may be an ester of a fatty acid for example a C12–C15 alkyl benzoate, a medium to long chain alcohol, an aromatic and/or alkyl pyrollidinone, an aromatic and/or alkyl, and/or cyclic ketone, an aromatic and/or alkyl, and/or cyclic ether, substituted and/or unsubstituted single or multiple ring aromatic, straight chain and/or branched chain and/or cyclic alkane or silicone. The organic cosolvent may be present in amounts of approximately 0.25% to 50% by weight, preferably 0.5 to 2% by weight, based on the total weight of the pharmaceutical mousse composition. Preferred organic cosolvents include C12–C15 alkyl benzoates (FINSOLV TN) and caprylic/capric triglyceride (CRODAMOL GTCC).

The pharmaceutical mousse composition according to the present invention may also contain other non-essential ingredients. The composition may contain up to 10 weight percent of conventional pharmaceutical adjuvants. These adjuvants or additives include preservatives, stabilisers, antioxidants, pH adjusting agents, skin penetration enhancers, and viscosity modifying agents.

EXAMPLES

The present invention will now be more fully described with reference to the accompanying figures and examples. It should be understood that the description following is illustrative only and should not be taken in any way as restrictive on the generality of the foregoing description.

Example 1

Formulations

Figure 1:
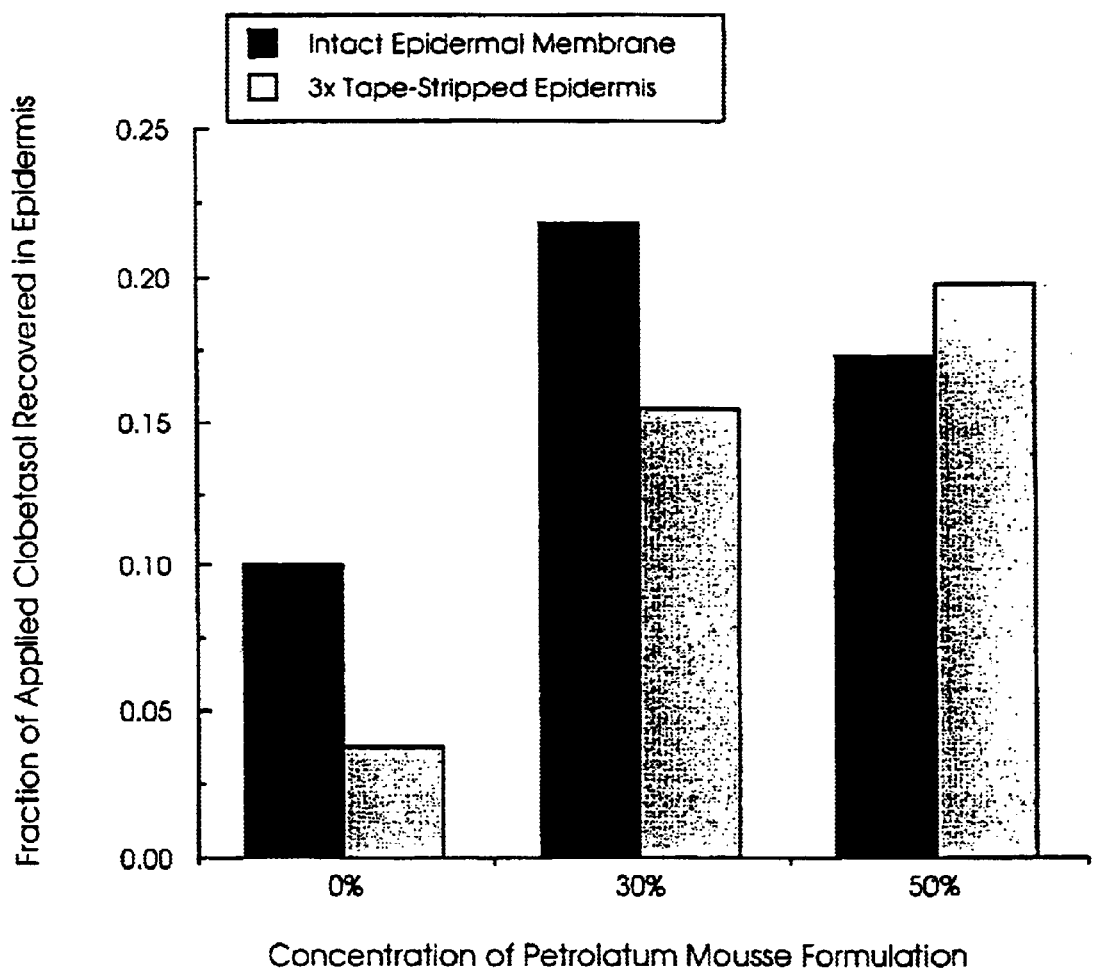
FIG. 1 illustrates the effect of petrolatum content on in vitro epidermal penetration of clobetasol from topical mousse formulations 72 hours after application of 10 mg/cm$^2$ of formulation.

A series of 7 pharmaceutical formulations were prepared in accordance with the present invention. The composition of each formulation is given in Table 1.

TABLE 1

| Ingredient | 1 | 2 | 3 | 4 | 5 | 6 | 7 |
| --- | --- | --- | --- | --- | --- | --- | --- |
| Petrolatum | 10% | 10% | 20% | 30% | 30% | 40% | 50% |
| Clobetasol Propionate | 0.05% | 0.05% | 0.05% | 0.05% | 0.05% | 0.05% | 0.05% |
| Capylic/Capric Triglyceride | — | — | — | — | 10% | — | — |
| Alkyl Benzoate | 10% | 10% | 10% | 10% | — | 10% | 10% |
| Cetearyl glucoside | 2.5% | — | — | — | — | — | — |
| Sorbitan Stearate | — | 1.63% | 2.54% | 3.44% | 3.02% | 4.35% | 5.25% |
| Polysorbate 60 | — | 2.37% | 3.46% | 4.56% | 4.98% | 5.65% | 6.75% |
| Water | 72.25% | 70.95% | 58.95% | 46.95% | 46.95% | 34.95% | 22.95% |
| Preservatives | 0.2% | — | — | — | — | — | — |
| Propellant | 5% | 5% | 5% | 5% | 5% | 5% | 5% |

Example 2

Effect of Petrolatum Concentration on the In-vitro Epidermal Penetration of Clobetasol from Topical Mousse Formulations Aim The aim of the study was to:
(1) determine the penetration of the steroid clobetasol into human epidermis following topical application of mousse formulations to which increasing concentrations of petrolatum had been included as a potential occlusive agent and penetration enhancer.
(2) To assess clobetasol penetration following application to intact epidermis and that which had been stripped 3 times with tape to model the impaired stratum corneum barrier function seen in the dermatological conditions for which the drug is used clinically.

Method

Preparation of epidermal membranes: Donated human female abdominal skin was separated by blunt dissection, to remove subcutaneous fat and extraneous tissue, and immersed in water at 60° C. for 2 minutes to allow separation of the epidermal-dermal junction. Epidermal membranes were lifted from the dermis by gently rolling from one end with the fingers and stored on filter paper, stratum corneum uppermost, at −20° C. until use.

Diffusion Studies Epidermal membranes were mounted, stratum corneum uppermost and facing the donor chamber, on filter paper between the two halves of standard horizontal glass Franz-type diffusion cells (area approx. 1.3 $cm^2$). The bottom half of the diffusion cells was filled with approximately 3.5 ml of receptor medium (either 20% ethanol in distilled water for intact epidermal membrane studies or Baxter 20% Intralipid® solution for stripped skin studies) and continuously stirred with small magnetic fleas. Assembled cells were semi submerged in a water bath maintained at 35±0.1° C.

Mousse formulations containing 0.05% clobetasol with the inclusion of 0, 30 or 50% petrolatum were gently applied to the donor chamber with a round-ended plastic rod which was wiped around the skin surface such that the skin was covered by a total dose of approximately 10 mg/$cm^2$. The weight of formulation applied was verified from the difference in weight of the application rod and small weigh boat from which the formulation had been applied before and after dosing.

Clobetasol was allowed to penetrate into the epidermis for 72 hrs after which time the remaining formulation was removed from the skin surface by washing and a single tape strip was performed to ensure that minimal 'unpenetrated' material remained on the surface of the epidermis. All washes and tape strips were retained for quantification of clobetasol concentration. The area of epidermis exposed to the formulation was then removed from the membrane using a stainless steel punch which was cleaned with methanol between samples to avoid any cross contamination of clobetasol. Epidermal, tape and wash samples were all assayed for clobetasol concentration by high performance liquid chromatography.

Results

FIG. 1 shows the fraction of the applied amount of clobetasol that was found to have penetrated into the epidermal membranes during the study. It can be clearly seen that inclusion of petrolatum in the mousse formulations has increased the amount of clobetasol penetrating into the epidermis of both intact and stripped skin samples. The recovery of the applied amounts of clobetasol in the washes, tape strip and epidermis was greater than 75% in all cases.

Conclusion

Increasing concentrations of petrolatum in topical mousse formulations containing 0.05% clobetasol was able to increase the in-vitro human epidermal penetration of the steroid in both intact and stripped skin models.

Example 3a

The Effect of Petrolatum Concentration on the Occlusivity of Topical Mousse Formulations Aim The aim of the study was to determine whether increasing the concentration of petrolatum in topical mousse formulations could effectively occlude the underlying skin and thereby lead to increased local hydration which in turn is known to improve the percutaneous penetration of suitable drugs.

Method

Relative degrees of occlusion of the skin in humans can be effectively quantified by following changes in the normal rate of transepidermal water loss (TEWL) caused by procedures such as formulation application. In the present study a commercially available single probe TEWL meter (Tewameter, Courage and Khazaka, Cologne, Germany) was used to determine the rate of TEWL (g/hr/$m^2$) at a number of 2×2 cm numbered test squares marked on the medial side of the forearm of a healthy volunteer. Baseline readings of TEWL were taken in triplicate at each test site prior to the application of mousse formulation at a dose of 10 mg/$cm^2$ containing 0, 10, 20, 30, 40 or 50% petrolatum. To ensure that the dose rate of 10 mg/$cm^2$ was maintained for each formulation, approximately 40 mg of each mousse was weighed out onto a 2 cm wide glass slide which was then used to wipe the mousse evenly across each one of the marked test squares before being reweighed to determine the total amount of mousse transferred onto the skin.

At 30 and 120 minutes following mousse application determinations of TEWL were repeated at each of the test sites. Relative changes in TEWL were then calculated by dividing the rate of TEWL following application by that taken from the same marked square at t=0.

Results

Figure 2:
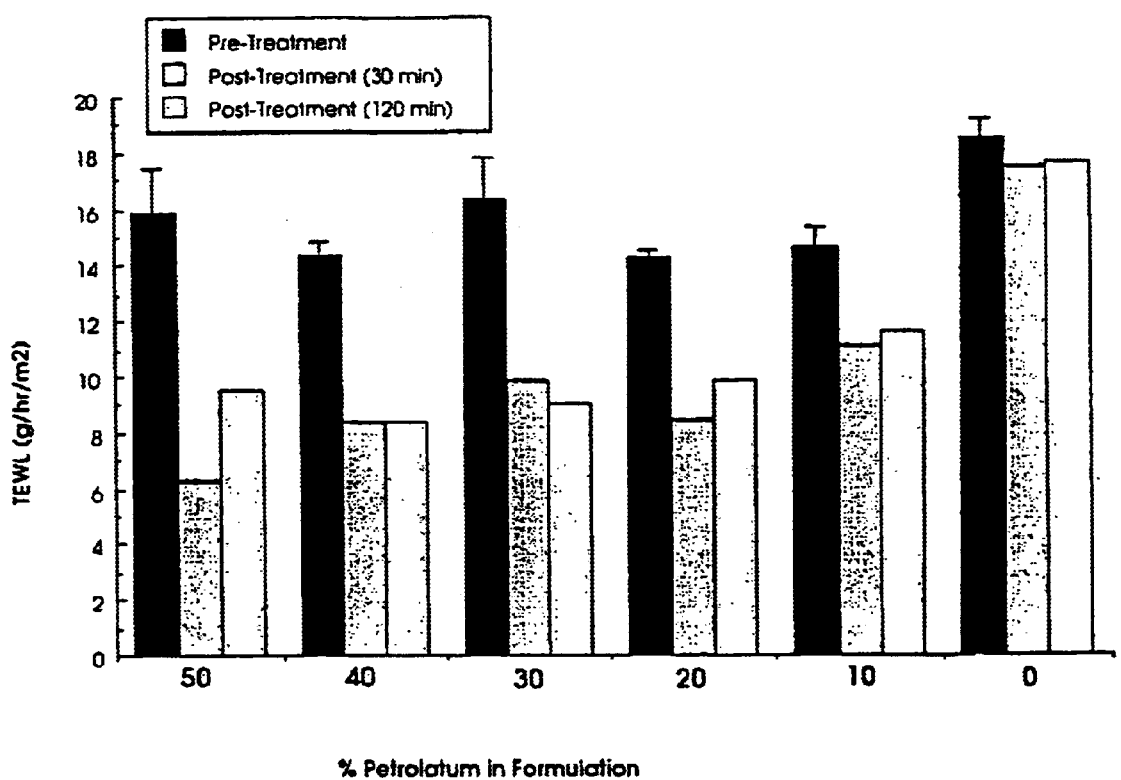
FIG. 2 illustrates the effect of petrolatum content on the rate of transepidermal water loss (TEWL) determined on the forearm of a healthy volunteer 30 and 120 minutes after topical application of 10 mg/cm$^2$ of formulation.
Figure 3:
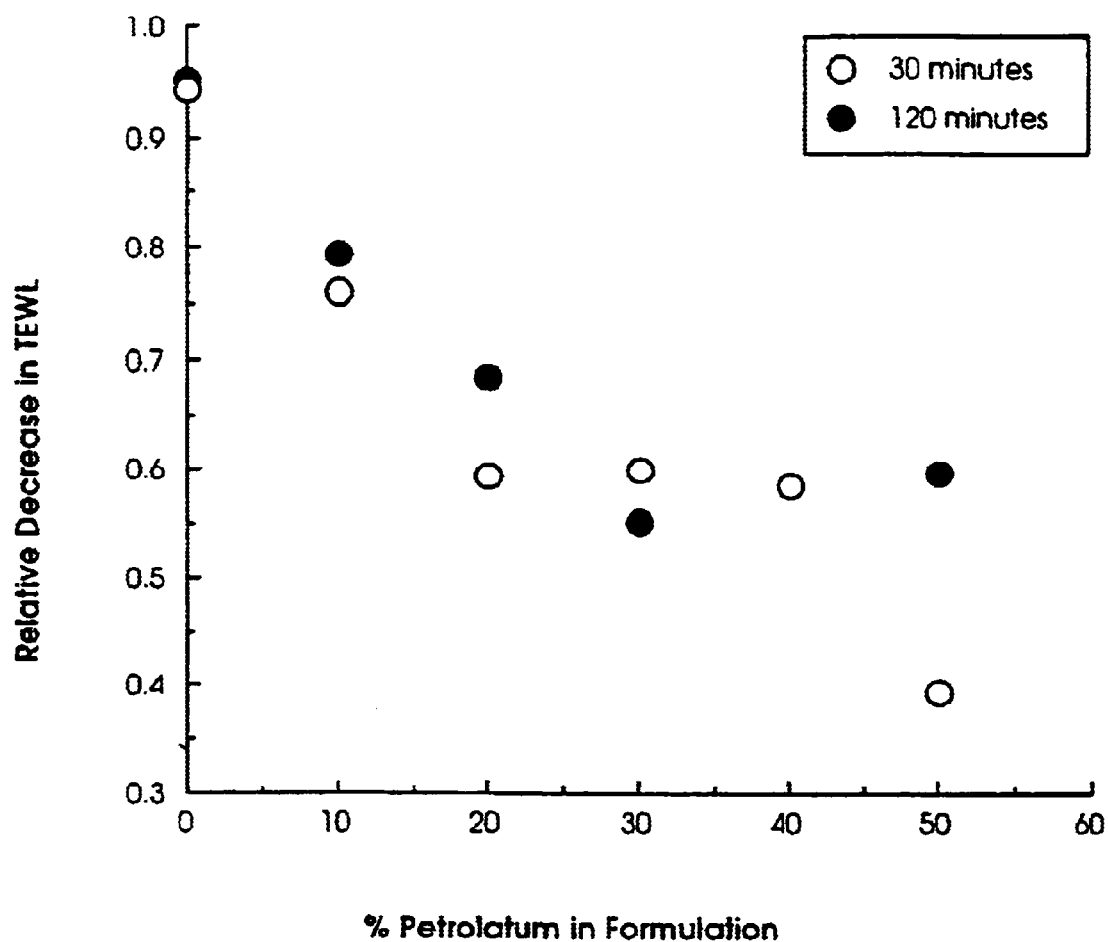
FIG. 3 illustrates relative decreases in the rate of transepidermal water loss (TEWL) observed on the forearm of a healthy volunteer with increasing concentrations of petrolatum in topically applied formulations.

FIG. 2 shows the actual rate of TEWL (g/hr/$m^2$) determined at each of the test sites prior to treatment and again at 30 and 120 minutes after mousse application. A decrease in the rate of TEWL was observed with increasing concentrations of petrolatum in the mousse formulations at both 30 and 120 minutes following application. FIG. 2 clearly shows the relationship between the % of petrolatum content in each of the test mousses and the resultant relative change in the rate of TEWL determined at 30 and 120 minutes after formulation application.

Conclusion

Increasing the concentration of petrolatum in topical mousse formulations was able to decrease the normal rate of TEWL on the forearm of a healthy volunteer. The decreases in the rate TEWL observed effectively demonstrate that increasing the concentration of petrolatum in the product leads to an increase in the relative occlusivity of the topical mousse formulations tested.

Example 3b

Part 2

Aim

The aim of the second part of this study was to assess the degree of occlusivity afforded by the 50% petrolatum mousse formulation in a number of healthy volunteers.

Method

The effect of a 10 mg/cm² dose of 50% mousse formulation on the normal rate of TEWL was determined on the forearm of 6 volunteers in a manner identical to that described above. The relative changes observed in the rate of TEWL at 30 and 120 min after application were then compared to an untreated control site measured at the same time on the tested forearm of each volunteer.

Results

Figure 4:
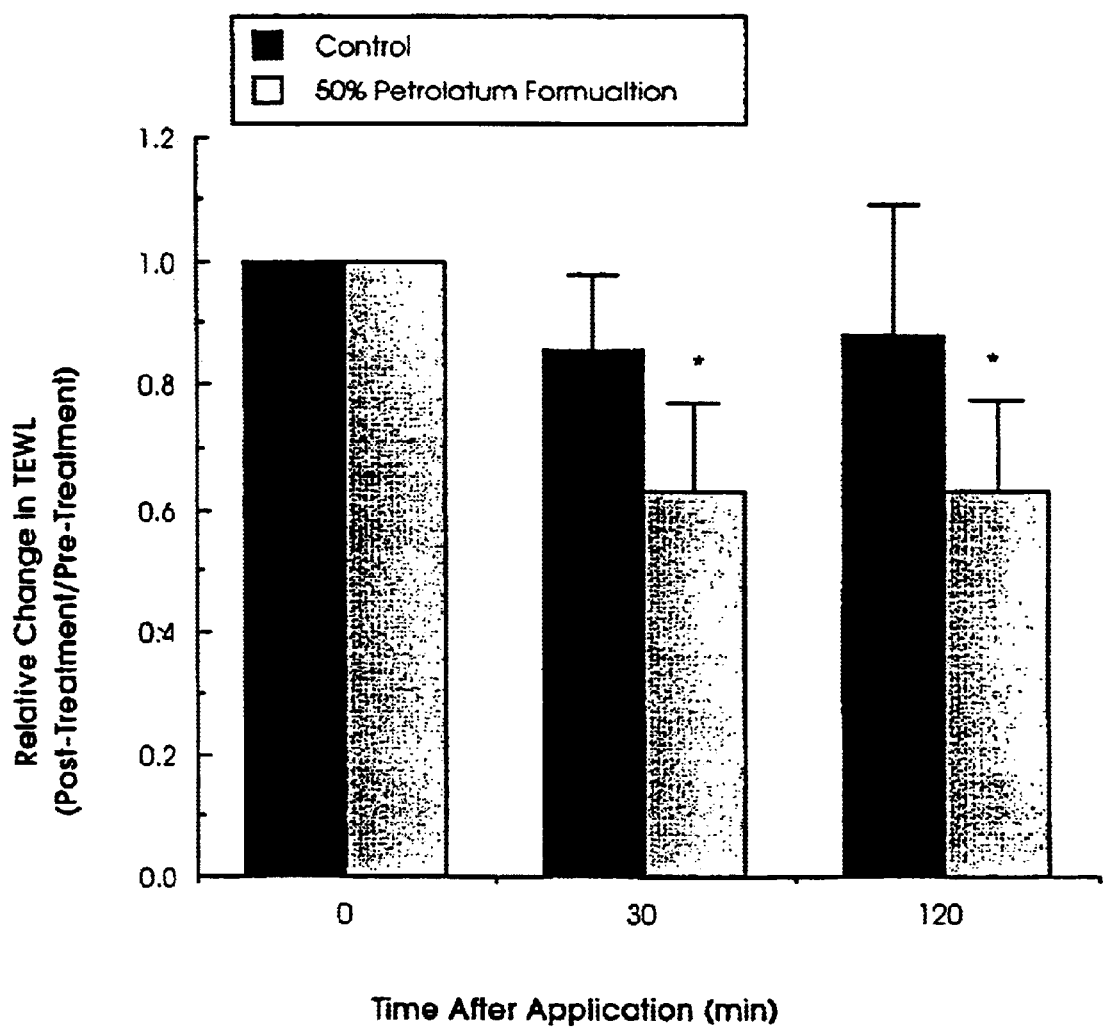
FIG. 4 illustrates the effect of application of a 50% petrolatum mousse formulation on the relative rate of TEWL on the forearm of healthy volunteers (mean±SD, n=6).

FIG. 4 shows the relative rates of TEWL determined at the 2 test sites on the forearms of the volunteers. Significant decreases in TEWL (P<0.05, ANOVA and Students t-test) were observed at both the 30 and 120 min post-treatment tests following application of the 50% petrolatum mousse formulation. No significant difference was observed in the rate of TEWL between the control sites over the 120 min test period (P=0.19, ANOVA).

Conclusion

Application of a mousse formulation containing 50% petrolatum at a dose of 10 mg/cm² significantly occluded the skin as determined by decreases in the rate of TEWL observed on the forearms of 6 healthy volunteers.

Finally, it is to be understood that various alterations, modifications and/or additions may be made without departing from the spirit of the present invention as outlined herein.

What is claimed is:

1. A pharmaceutical aerosol foam composition comprising:
   an effective amount of a pharmaceutically active ingredient;
   an occlusive agent;
   an aqueous solvent;
   an organic cosolvent; and
   an emulsifier component in an amount wherein the ratio of emulsifier component to a combination of the occlusive agent, pharmaceutically active ingredient, and organic cosolvent is about 1:5 to about 1:8;
   the pharmaceutically active ingredient being insoluble in both water and the occlusive agent;
   the occlusive agent being present in an amount sufficient to form an occlusive layer on the skin, in use.

2. The pharmaceutical aerosol foam composition according to claim 1, wherein the occlusive agent is petrolatum.

3. The pharmaceutical aerosol foam composition according to claim 1, wherein the occlusive agent is selected from the group consisting of a mineral oil and grease, a long chain acid, an animal fat and grease, a vegetable fat and grease and a water insoluble polymer.

4. The pharmaceutical aerosol foam composition according to claim 1 or claim 2, wherein the pharmaceutically active ingredient is present in an amount of from approximately 0.005% by weight to approximately 10% by weight, based on the total weight of the pharmaceutical aerosol foam composition.

5. The pharmaceutical aerosol foam composition according to claim 1 or claim 2, wherein the emulsifier component is present in an amount of from approximately 1 to 15% by weight, based on the total weight of the composition.

6. The pharmaceutical aerosol foam composition according to claim 1 or claim 2, wherein the aqueous solvent is present in an amount of from approximately 25 to 95% by weight, based on the total weight of the composition.

7. The pharmaceutical aerosol composition according to claim 1 or claim 2, wherein the organic cosolvent is present in an amount from approximately 0.25% by weight to 50% by weight, based on the total weight of the composition.

8. The pharmaceutical aerosol foam composition according to claim 7 wherein the organic cosolvent is an alkyl benzoate.

9. The pharmaceutical aerosol foam composition according to claim 1 or claim 2, further including an effective amount of an aerosol propellant.

10. The pharmaceutical aerosol foam composition according to claim 9, wherein the aerosol propellant is a hydrocarbon and is present in an amount of from approximately 2.5 to 20% by weight, based on the total weight of the composition.

11. The pharmaceutical aerosol foam composition according to claim 1 or claim 2, wherein the occlusive agent is present in an amount of approximately 55% by weight or less, based on the total weight of the composition.

12. The pharmaceutical aerosol foam composition according to claim 11, wherein the occlusive agent is present in an amount of approximately 10 to 50% by weight, based on the total weight of the composition.

13. The pharmaceutical aerosol foam composition according to claim 1 or claim 2, wherein the emulsifier component is selected from the group consisting of a non-ionic, cationic or anionic surfactant, a fatty alcohol, a fatty acid and fatty acid salts thereof.

14. The pharmaceutical aerosol foam composition according to claim 13, wherein the emulsifier component includes a mixture of a sorbitan ester and a polyoxyethylene fatty alcohol ether.

15. The pharmaceutical foam composition according to claim 1 or claim 2, wherein the water insoluble pharmaceutically active ingredient is selected from the group consisting of an analgesic, anti-inflammatory agent, antifungal, antibacterial, anesthetic, xanthine, sex hormone, antiviral, antipruritic, antihistamine and corticosteroid.

16. The pharmaceutical aerosol foam composition according to claim 15, wherein the pharmaceutically active ingredient is a corticosteroid selected from the group consisting of betamethasone valerate and clobetasol propionate.

17. The pharmaceutical aerosol foam composition according to claim 15, wherein the pharmaceutically active ingredient is a corticosteroid selected from one or more of the group consisting of betamethasone valerate and clobetasol propionate.

18. A pharmaceutical aerosol dispenser comprising: a pharmaceutical aerosol foam composition including
   an effective amount of a pharmaceutically active ingredient;
   an occlusive agent;
   an aqueous solvent;
   an organic cosolvent; and
   an emulsifier component in an amount wherein the ratio of emulsifier component to a combination of the occlusive agent, pharmaceutically active ingredient, and organic cosolvent is about 1:5 to about 1:8;
   the pharmaceutically active ingredient being insoluble in both water and the occlusive agent;
   the occlusive agent being present in an amount sufficient to form an occlusive layer on the skin, in use.

19. A pharmaceutical aerosol foam composition consisting essentially of:
   an effective amount of a pharmaceutically active ingredient;
   an occlusive agent;
   an aqueous solvent;
   an organic cosolvent; and the pharmaceutically active ingredient being insoluble in both water and the occlusive agent;

the occlusive agent being present in an amount sufficient to form an occlusive layer on the skin, in use.

20. The pharmaceutical aerosol foam composition according to claim 19, wherein the occlusive agent is petrolatum.

21. The pharmaceutical aerosol foam composition according to claim 19, wherein the occlusive agent is selected from the group consisting of a mineral oil and grease, a long chain acid, an animal fat and grease, a vegetable fat and grease and a water insoluble polymer.

22. The pharmaceutical foam composition according to claim 19 or claim 20, wherein the water insoluble pharmaceutically active ingredient is selected from the group consisting of an analgesic, an anti-inflammatory agent, an antifungal, an antibacterial, an anesthetic, a xanthine, a sex hormone, an antiviral, an antipruritic, an antihistamine and a corticosteroid.

23. The pharmaceutical aerosol foam composition according to claim 19 or claim 20, wherein the pharmaceutically active ingredient is present in amounts of from approximately 0.005% by weight to approximately 10% by weight, based on the total weight of the pharmaceutical aerosol foam composition.

24. The pharmaceutical aerosol foam composition according to claim 19 or claim 20, wherein the occlusive agent is present in an amount of approximately 55% by weight or less, based on the total weight of the composition.

25. The pharmaceutical aerosol foam composition according to claim 24, wherein the occlusive agent is present in an amount of approximately 10 to 50% by weight, based on the total weight of the composition.

26. The pharmaceutical aerosol foam composition according to claim 19 or claim 20, wherein the aqueous solvent is present in an amount of from approximately 25 to 95% by weight, based on the total weight of the composition.

27. The pharmaceutical aerosol composition according to claim 19 or claim 20, wherein the organic cosolvent is present in an amount from approximately 0.25% by weight to 50% by weight, based on the total weight of the composition.

28. The pharmaceutical aerosol foam composition according to claim 27 wherein the organic cosolvent is an alkyl benzoate.

29. The pharmaceutical aerosol foam composition according to claim 19 or 20, further including an effective amount of an aerosol propellant.

30. The pharmaceutical aerosol foam composition according to claim 29, wherein the aerosol propellant is a hydrocarbon and is present in an amount of from approximately 2.5 to 20% by weight, based on the total weight of the composition.

31. The pharmaceutical aerosol foam composition according to claim 19 or claim 20, further including an effective amount of an emulsifier component.

32. The pharmaceutical aerosol foam composition according to claim 31, wherein the emulsifier component is present in an amount of from approximately 1 to 15% by weight, based on the total weight of the composition.

33. The pharmaceutical aerosol foam composition according to claim 31, wherein the emulsifier component is selected from the group consisting of a non-ionic, cationic or anionic surfactant, a fatty alcohol, a fatty acids and fatty acid salts thereof.

34. The pharmaceutical aerosol foam composition according to claim 33, wherein the emulsifier component includes a mixture of a sorbitan ester and a polyoxyethylene fatty alcohol ether.

35. A pharmaceutical aerosol dispenser comprising a pharmaceutical aerosol foam composition, said composition consisting essentially of:

an effective amount of a pharmaceutically active ingredient an occlusive agent;

an aqueous solvent;

an organic cosolvent; and the pharmaceutically active ingredient being insoluble in both water and the occlusive agent;

the occlusive agent being present in an amount sufficient to form an occlusive layer on the skin, in use.

36. The pharmaceutical aerosol dispenser of claim 35, wherein said foam composition further includes an effective amount of an emulsifier component.

37. A pharmaceutical aerosol foam composition comprising:

an effective amount of a corticosteroid;

an occlusive agent;

an aqueous solvent;

an organic cosolvent; and the pharmaceutically active ingredient being insoluble in both water and the occlusive agent;

the occlusive agent being present in an amount sufficient to form an occlusive layer on the skin, in use.

38. The pharmaceutical aerosol foam composition according to claim 37, further comprising an emulsifier component in an amount of from approximately 1 to 15% by weight, based on the total weight of the composition.

39. A pharmaceutical aerosol foam composition comprising:

an occlusive agent in an amount up to 50% by weight, based on the total weight of the composition;

an aqueous solvent;

an organic cosolvent, an effective amount of clobetasol propionate, wherein said clobetasol propionate is solubilized in the composition.

40. A pharmaceutical aerosol foam composition comprising:

petrolatum in an amount of approximately 10 to 50% by weight, based on the total weight of the composition;

an aqueous solvent;

an organic cosolvent, an effective amount of clobetasol propionate, wherein said clobetasol propionate is solubilized in the composition.

* * * * *